US008467865B2

(12) United States Patent
Gregory et al.

(10) Patent No.: US 8,467,865 B2
(45) Date of Patent: Jun. 18, 2013

(54) METHOD FOR DETECTING BOTH PRE-CANCEROUS AND CANCEROUS TISSUES

(75) Inventors: William D. Gregory, Shorewood, WI (US); Christopher W. Gregory, Tucson, AZ (US)

(73) Assignee: WiSys Technology Foundation, Madison, WI (US)

( * ) Notice: Subject to any disclaimer, the term of this patent is extended or adjusted under 35 U.S.C. 154(b) by 756 days.

(21) Appl. No.: 12/042,425

(22) Filed: Mar. 5, 2008

(65) Prior Publication Data

US 2008/0221475 A1    Sep. 11, 2008

Related U.S. Application Data (60) Provisional application No. 60/905,081, filed on Mar. 5, 2007.

(51) Int. Cl.
*A61B 5/05* (2006.01)
(52) U.S. Cl.
USPC .......................................................... 600/547
(58) Field of Classification Search
USPC ................................. 600/547, 587
See application file for complete search history.

(56) References Cited

U.S. PATENT DOCUMENTS

| 6,532,384 | B1 * | 3/2003 | Fukuda | 600/547 |
| 2006/0270942 | A1 * | 11/2006 | McAdams | 600/547 |
| 2007/0203425 | A1 * | 8/2007 | Woo et al. | 600/547 |

OTHER PUBLICATIONS

Dittmar et al, New Equations for Estimating Body Cell Mass from Bioimpedance Parallel Models in Healthy Older Germans, Am J Physiol Endocrinol Metab 281: E1005-E1014, 2001, pp. E1005-E1014.*
Hope et al, Technology review: The use of electrical impedance scanning in the detection of breast cancer, Breast Cancer Res 2004, 6:69-74.*

* cited by examiner

*Primary Examiner* — Brian Szmal
(74) *Attorney, Agent, or Firm* — Quarles & Brady, LLP (57) ABSTRACT

A method for characterizing tissues within a subject as cancerous or non-cancerous includes determining the electrical properties of the subject. The electrical properties of the subject are fit to a model and a characteristic frequency of each tissue is then calculated. Each tissue is finally characterized as cancerous or non-cancerous if its characteristic frequency lies above a threshold value.

16 Claims, 6 Drawing Sheets

METHOD FOR DETECTING BOTH PRE-CANCEROUS AND CANCEROUS TISSUES

CROSS-REFERENCE TO RELATED APPLICATIONS

This application claims the benefit of U.S. Provisional patent application Ser. No. 60/905,081 filed on Mar. 5, 2007 and entitled "A Novel Method and Apparatus to Detect Both Pre-cancerous and Cancerous Cells".

BACKGROUND OF THE INVENTION

The field of the invention is electrical property measurement and imaging systems, and methods related thereto. More particularly, the invention relates to characterizing a tissue as cancerous or non-cancerous using the measured electrical characteristics of the tissue.

Screening mammography has been the gold standard for breast cancer detection for over 30 years, and is the only available screening method proven to reduce breast cancer mortality. However, the sensitivity of screening mammography varies considerably. The most important factor in the failure of mammography to detect breast cancer is radiographic breast density. In studies examining the sensitivity of mammography as a function of breast density, the sensitivity of mammography falls from 87-97 percent in women with fatty breasts to 48-63 percent in women with extremely dense breasts. Additional drawbacks of conventional mammographic screening include patient discomfort associated with the compression of the breast. Diagnostic alternatives to mammography include ultrasound and MRI. The effectiveness of whole-breast ultrasound as a screening technique, however, does not appear to be significantly different from mammography. Furthermore, while MRI has an apparent increased sensitivity for the detection of breast cancer and is not affected by breast density, the high cost of bilateral breast MRI (approximately 20 times more expensive than mammography) has precluded its widespread use as a screening technique.

A high percentage of breast cancers are not detected at the screening stage. Studies show that 20-50% of breast cancers go undetected at the screening stage. In fact, it is estimated that by the time a tumor is detected by mammography it has been already been growing for upwards of 5-8 years. The motivation for early detection is great: when an invasive breast cancer is discovered at a small size, it is less likely to have metastasized and more likely correspond to a higher survival rate. For example, breast cancer detected in the early stage has a 5 year survival rate of approximately 96%, while the 5 year survival rate for late stage breast cancer falls to 20%.

After a suspicious lesion is found, medical professionals often rely on expensive biopsies to determine cancerous tissues. These procedures are neither fast nor patient-friendly. Surgical biopsy is recommended for suspicious lesions with a high chance of malignancy but fine-needle aspiration cytology (FNAC) and core biopsy can be inexpensive and effective alternatives. Both FNAC and core biopsy have helped to reduce the number of surgical biopsies, sparring patients anxiety and reducing the cost of the procedure. However, core biopsies have often failed to show invasive carcinoma and both FNAC and core biopsies can result in the displacement of malignant cells away from the target, resulting in misdiagnosis. Additionally, core biopsies have a limited sampling accuracy because only a few small pieces of tissue are extracted from random locations in the suspicious mass. In some cases, sampling of the suspicious mass may be missed altogether. Consequences include a false-negative rate of 1-7% (when verified with follow up mammography) and repeat biopsies (percutaneous or surgical) in 9-18% of patients (due to discordance between histological findings and mammography). The sampling accuracy of core needle biopsy is, furthermore, highly dependent on operator skills and on the equipment used.

Transforming growth factor beta (TGF-$\beta$) has long been known to have a role in the proliferation and cellular differentiation of many cell types, including breast tissue. Decreases in the TGF-$\beta$ co-receptor TGF $\beta$RIII have recently been shown to correlate with the likelihood that a breast tissue will develop into malignant cancer. Moreover, the loss of TGF $\beta$RIII expression occurs early in the progression of cells from normal to cancerous, and is present in non-invasive stages of breast cancer such as ductal carcinoma in situ (DCIS). Therefore, determining the levels of TGF $\beta$RIII appears to be able to serve as an early indicator for breast tissue that is prone to develop into malignant cancer. Such a determination, however, would necessarily be done ex vivo on a biopsied tissue sample.

The characterization of cancerous tissue is divided into two groups: in situ and infiltrating lesions. In situ lesions are tumors that remain confined in epithelial tissue from which they originated. The tumor does not cross the basal membrane, thus the tumor and the healthy tissue are of the same nature (epithelial). The electrical impedance of an in situ lesion is thus dependent on the abundance of the malignant cells that will impact the macroscopic conductivity (which is influenced by the increase in sodium and water) and permittivity (which is influenced by the difference in cell membrane electrochemistry).

By contrast, infiltrating lesions are tumors that pass through the basal membrane. The malignant tissue has a different nature than normal tissue (epithelial vs. adipose). Epithelial tissue is compact and dense. Adipose tissue is composed of large cells that are mostly triglycerides. These structural differences have several impacts. First the normal tissue has a lower cellular density. Second, cell liquid of normal tissue is not as abundant as epithelial cells. Generally the radii of epithelial cells are less than adipose cells, indicating that the radius of cancerous cells is less than for normal cells. The impact on the fractional volume of cancerous cells versus normal cells is that the fractional volume of cancerous cells is greater than for normal cells. The reason for this is that the epithelial population is higher than for normal, adipose cells. Finally, the intracellular conductivity of cancerous cells is greater than for intracellular conductivity of normal cells. Moreover, the extracellular conductivity is higher because of the abundance of extracellular fluid (because of larger gaps between normal and cancerous cells). Thus, the conductivity of the infiltrated tissue will be greater than for normal tissue.

Electrical impedance tomography (EIT) is a process that maps the impedance distribution within an object. This map is typically created from the application of current and the measurement of potential differences along the boundary of that object. There are three categories of EIT systems: current injection devices, applied potential devices, and induction devices. Henderson and Webster first introduced a device known as the impedance camera that produced a general map of impedance distribution. The Sheffield System and its incarnations were the first generation EIT system. In the late 1980's, Li and Kruger report on an induced current device. In such a system, a combination of coils is placed around the object under test. A changing current in the coils produces a varying magnetic field that in turn induces a current in the object under test. As with the other drive method, electrodes are placed on the boundary of the object to measure the potential drops along the boundary.

Such electrical property imaging techniques are often referred to as "impedance tomography." Most conventional electrical property imaging techniques are based on the premises that: 1) electrodes, or sensors, should be attached directly to the sample to be measured (for medical applications, the sample is a human body), and 2) current is injected sequentially through each electrode into the sample and the subsequent voltages measured. Therefore, these conventional EIT imaging techniques implement a "constant current/measured voltage" scheme.

In a departure from such conventional electrical property imaging techniques, U.S. Pat. No. 4,493,039 disclosed a method in which sensors are arranged in an array outside the object to be measured and during imaging of a sample, AC voltages are applied at a fixed amplitude while the current is measured. This approach, which is sometimes referred to as electrical property enhanced tomography (EPET), was further improved upon as described in U.S. Pat. No. 6,522,910 by filling the space between the object and the sensor array with an impedance matching medium.

SUMMARY OF THE INVENTION

The present invention overcomes the aforementioned drawbacks by providing a method for characterizing regions in a subject as either cancerous or non-cancerous. More specifically, the present invention is a method for determining if the tissues in a region in a subject are cancerous or non-cancerous by measuring the electrical characteristics of the tissues and determining a characteristic frequency of the tissues by fitting the electrical characteristics to a model. This method provides a fast, accurate, inexpensive, and non-painful alternative to the previous methods of cancer detection within a subject.

In general, the invention is practiced on the breast as a means of determining regions of the breast that are cancerous or non-cancerous; however, the present invention could also be practiced on other regions of the body as well as on animals. The characterization process is carried out by fitting information of the electrical properties of the breast to a model of the impedance of a tissue. From this model, a characteristic frequency of the tissue under examination is determined and employed to characterize the tissue. Since cellular changes corresponding to the development of cancer can occur before a tissue progresses into the later stages of malignant cancer, the present invention can detect incipient cancerous tissues that are otherwise characterized as non-cancerous by pathohistological examination. As a result, pre-cancerous tissues can be located and characterized without painful and invasive biopsy procedures. Moreover, the tissues within the breast can be characterized regardless of the density of the breast under examination.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

The present invention is practiced using a device configured to measure the electrical properties of an object. The following embodiments of the invention will be described wherein the object under examination is the human breast and the electrical properties of tissues within the breast are determined. It should be noted, however, that the present invention can be practiced on other parts of the body as well as on animals. The type of device utilized will depend on the particular application. For example, if the desire is to determine the electrical properties of a subject's breast in vivo, then an EPET device, such as the one described in co-pending U.S. patent application Ser. No. 11/857,493, which is incorporated herein by reference, is employed. However, if the electrical properties of a biopsied tissue sample from the breast are to be determined ex vivo, then a simple four-electrode device is employed.

Figure 5:
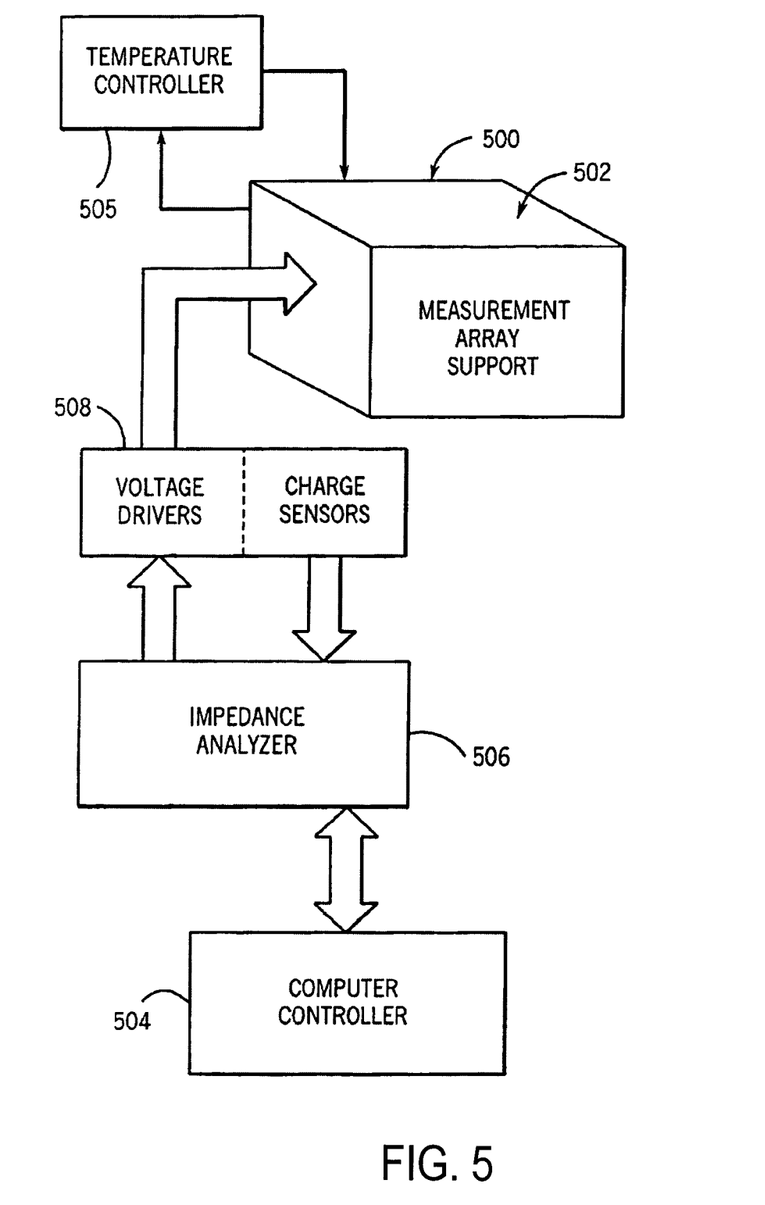
FIG. 5 is a block diagram of an electrical property imaging system that can be employed to practice the present invention.

Referring specifically now to FIG. 5, the EPET system is controlled by a computer controller 504. It operates an impedance analyzer 506 to apply voltages to the separate elements of a charge measurement array through voltage drivers 508, and it measures the resulting charge, Q, at each of these elements. One embodiment of an impedance analyzer 506 is commercially available from Solartron Analytical under the trade name "1260 Impedance/Gain Phase Analyzer". It is operated using the "Z plot" software produced by the Scribner Corporation. The "Z plot" software is run on the computer controller 504. To maintain the accuracy of the measurements, the temperature of a saline solution in the measurement array support structure 500 is controlled. This is accomplished by a temperature controller 505 which operates a heating element (not shown) in the support 500 in response to a signal received from a temperature sensor (not shown) which is also in the support 500. Preferably, the temperature is maintained at body temperature for the comfort of the patient.

Figure 6A:
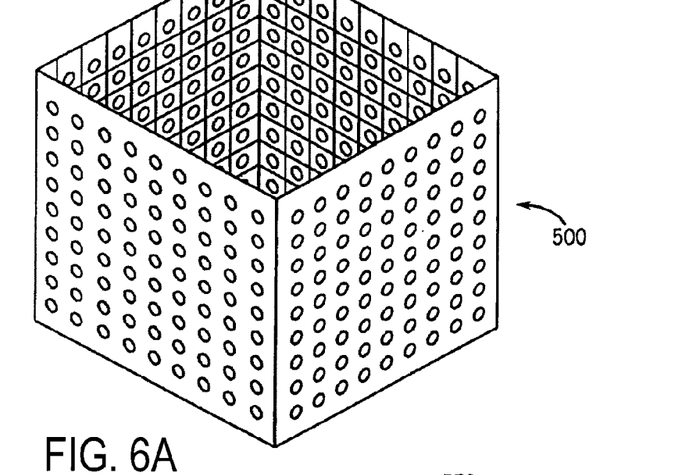
FIGS. 6A and 6B are schematic diagrams of one embodiment of a measurement array support which forms part of the system of FIG. 5.
Figure 6B:
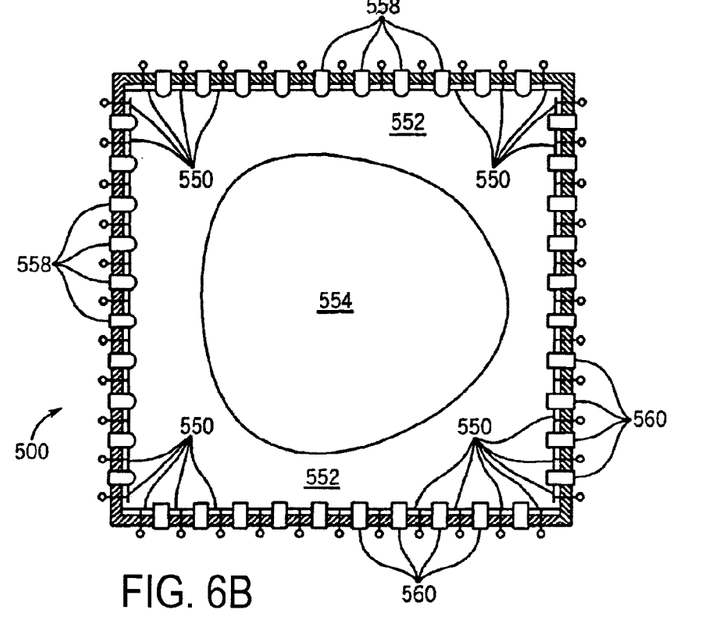

Referring particularly to FIGS. 6A and 6B, one embodiment of the measurement array support structure 500 includes 2D arrays of metal elements 550 disposed on all four sides of the container. These elements 550 are square metal electrodes that connect to the outputs 514 of corresponding voltage drivers 508. They are in electrical contact with the saline solution medium 552 that surrounds the subject 554. The voltages applied to these elements 550 establish an electric field, E, within the container and throughout the subject 554, and they accumulate a surface charge, $Q_j$, that is dependent on the electrical characteristics of the subject 554. In this embodiment 225 elements 550 are disposed on each of the four sides and they are constructed of silver with a silver chloride coating or blackened platinum.

Figure 1:
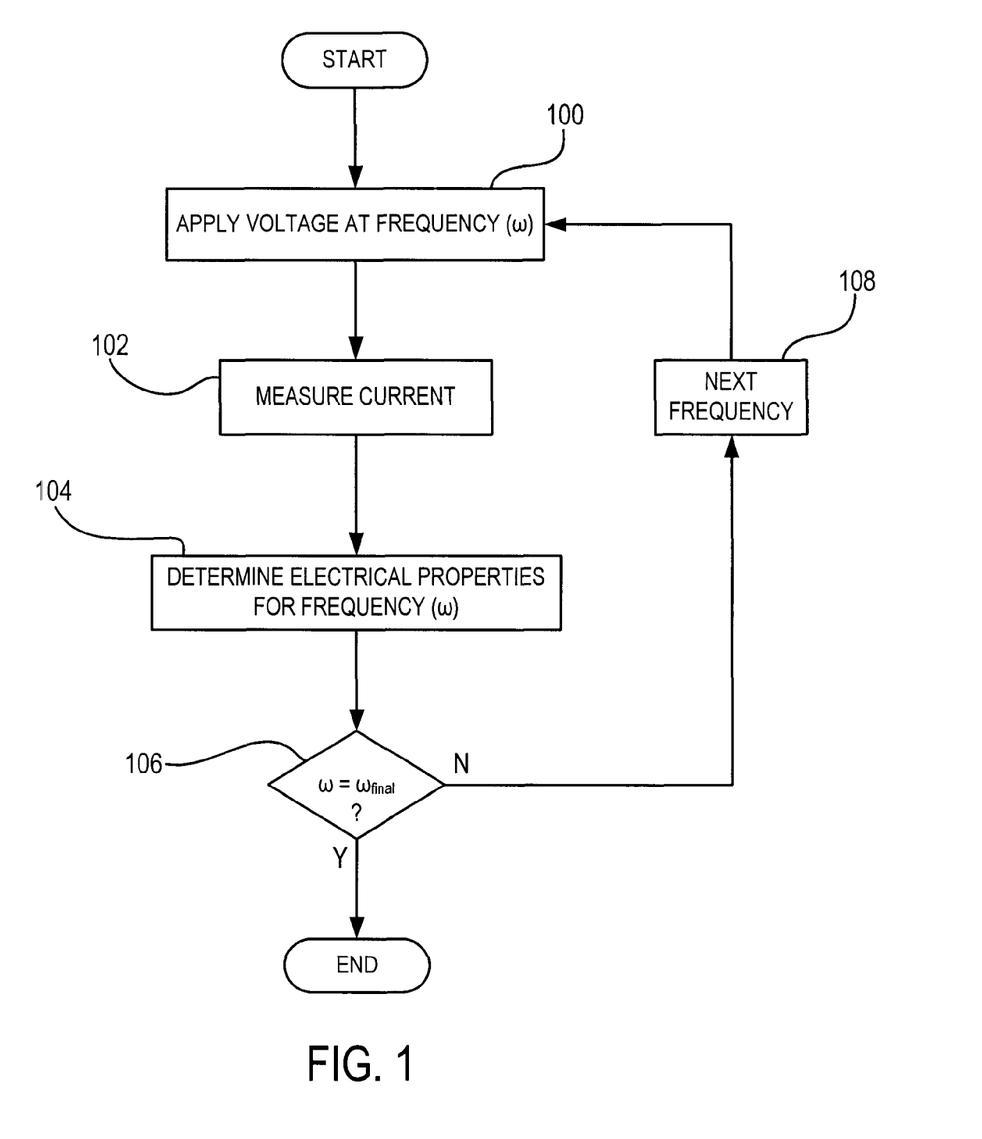
FIG. 1 is a flowchart depicting a method for measuring the electrical properties of a subject employing the device of FIGS. 5 and 6.

The EPET device described above is employed in the present invention to apply a voltage to electrodes on the surface of the object at a selected measurement frequency and data is acquired by measuring currents on the electrodes. Referring now to FIG. 1, a time-varying voltage, i.e., a voltage varying in magnitude over time, is applied to an array of electrodes in electrical contact with the surface of the breast, at a selected measurement frequency, as shown at step 100. Currents that result from this applied voltage are then measured in the array of electrodes, as indicated at step 102. These currents are expressed as charges (per unit time) on the sensor electrodes and are further related to the internal charges within the object. Since the internal charges only build up on the boundaries between two regions having different electrical properties, an anomaly within an object produces an electrical charge at the interface between the regions having different electrical properties. These charges, in turn, redistribute the charges on the electrodes in a manner that is mathematically unique in its relation to the internal charge distribution. Using the measured currents, then, the electrical properties throughout the breast are determined at step 104, as described in more detail in co-pending U.S. patent application Ser. No. 11/857,493. In the preferred embodiment of the present invention, the electrical properties determined are the impedances throughout the breast. Referring still to the measurements made in vivo with an EPET device, the electrical conductivities of two adjacent regions having different electrical properties are determined through the following relationship:

$$\delta q = \left(\frac{\sigma_2^* - \sigma_1^*}{\sigma_2^* + \sigma_1^*}\right)\left(\frac{-\varepsilon_0 \delta A}{2}\right) \cdot \hat{x} \cdot \nabla \Phi,$$

Where $\delta_q$ is the internal charge difference that builds up on the boundary between two regions having different electrical properties, $\sigma_1^*$ is the complex conductivity of a first adjacent region, $\sigma_2^*$ is the complex conductivity of a second adjacent region, $\varepsilon_0$ is the permittivity of free space, $\delta A$ is a differential area on the surface of the boundary between the first and second adjacent regions, and $\hat{x} \cdot \nabla \Phi$ is the electrical potential along the direction normal to the boundary. Since the complex conductivity, also called admittivity, of an object is related to the impedance of that object through the following proportion:

$$\overline{Z} \propto 1/\sigma^*,$$

The impedance values throughout the breast tissue are determined by first determining the complex conductivity of each region within the breast. The above-described measurement process is repeated at a plurality of selected measurement frequencies until current measurements have been made and impedance values determined at each selected measurement frequency. For example, measurement frequencies ranging from 10 kHz to 1 MHz may be employed. This loop concludes at decision block 106, with each subsequent measurement frequency being selected at step 108.

Figure 3:
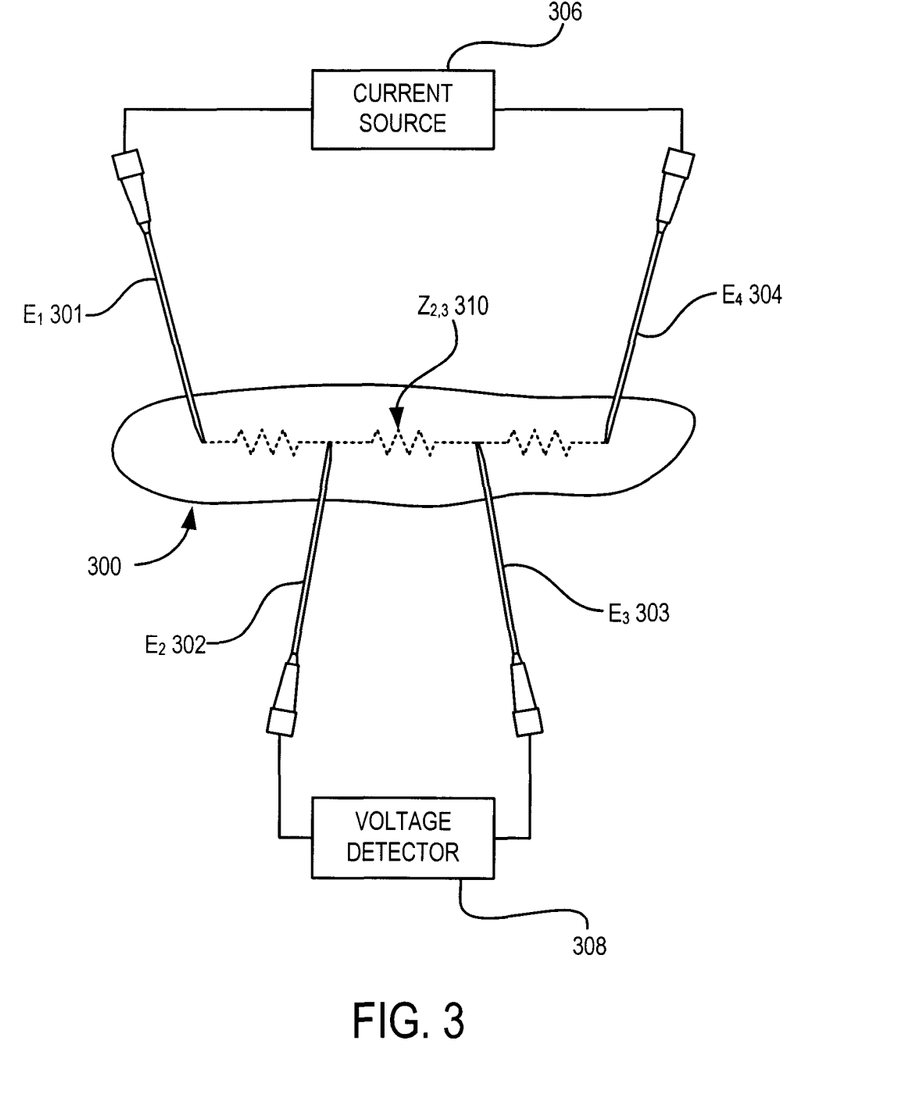
FIG. 3 is a schematic diagram of a measurement device that can be employed to practice the present invention.

An example of a four-electrode device employed to practice the present invention on a tissue sample ex vivo is shown in FIG. 3. Four electrodes are placed in electrical contact with the tissue sample 300 to be measured. Current from a current source 306 is supplied through electrodes $E_1$ 301 and $E_4$ 304. This current flows through the tissue sample 300 and a voltage is then produced and measured across electrodes $E_2$ 302 and $E_3$ 303, in general, with a voltage detector 308. The result of this arrangement is the measurement of the impedance, $Z_{2,3}$, 310 in the tissue sample 300 between electrodes $E_2$ 302 and $E_3$ 303.

Figure 2:
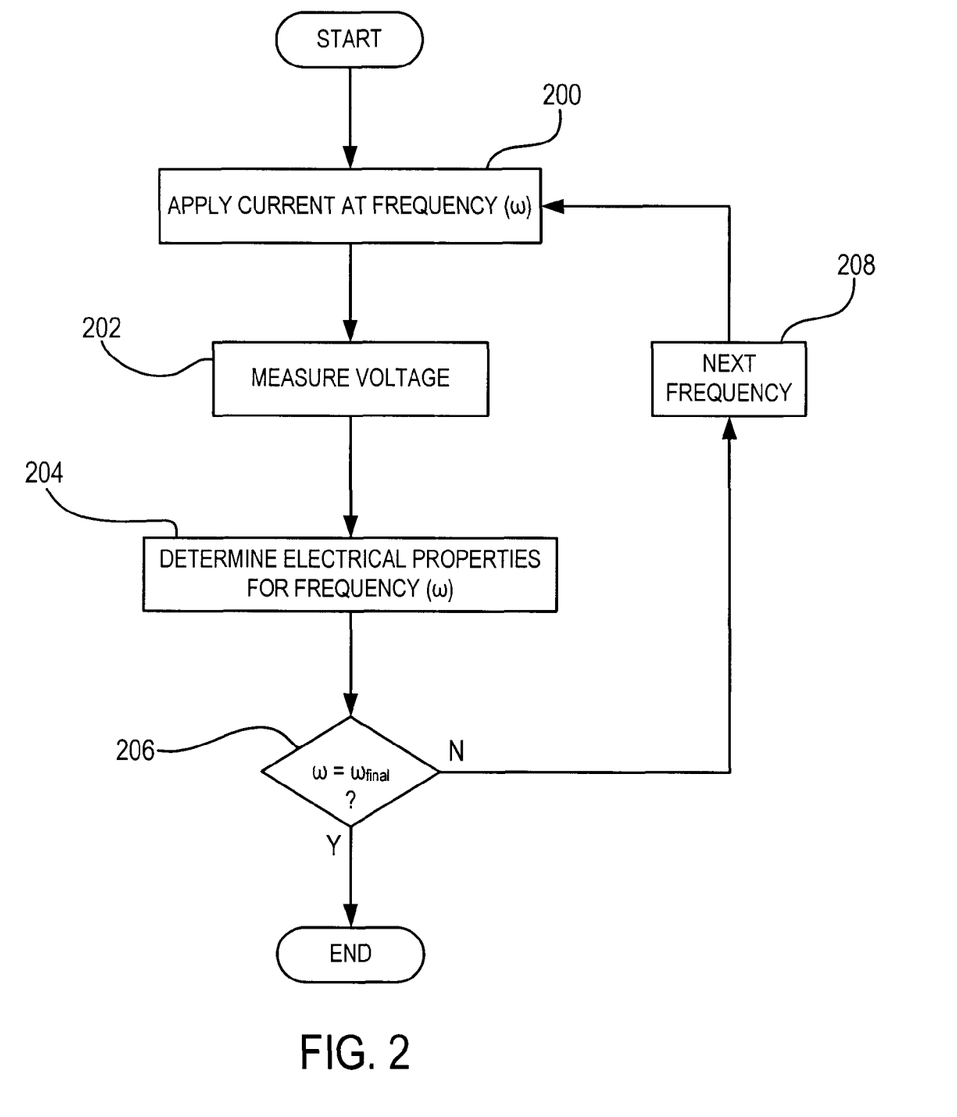
FIG. 2 is a flowchart depicting another method for measuring the electrical properties of a subject employing the device of FIG. 3.

The measurement process employing the four-electrode device is shown in FIG. 2, to which reference is herein made. A current from the current source 306 is first applied to the tissue sample 300 at a particular measurement frequency, ω, as indicated at step 200. The resultant voltage is then measured between electrodes $E_2$ 302 and $E_3$ 303 at step 202. The impedance 310 in the tissue sample 300 is then determined for the applied measurement frequency, as indicated at step 204. This process is repeated for a plurality of measurement frequencies until each desired frequency has been utilized. For example, measurement frequencies ranging from 1 Hz to 32 MHz may be employed; however, measurement frequencies can be alternatively selected up to 105 MHz. The decision whether all of the desired frequencies have been employed is made at step 206.

Figure 4:
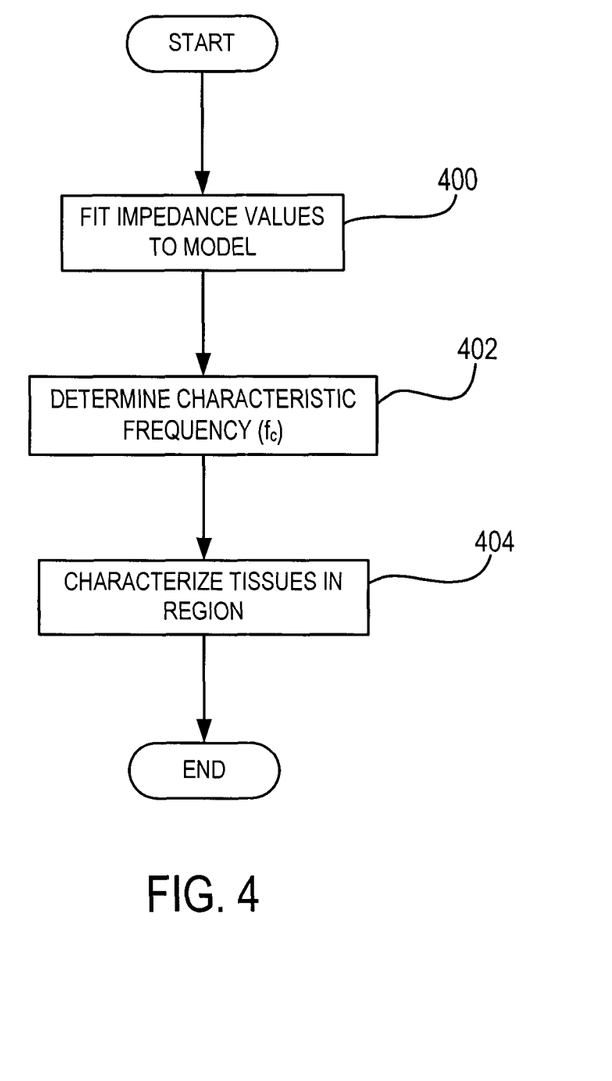
FIG. 4 is a flowchart depicting an embodiment of the method for practicing the present invention.

Referring particularly now to FIG. 4, the characterization process begins by fitting the measured impedance values for the tissues within the breast to a model, as indicated at step 400. In the preferred embodiment, the model employed is a Cole model, which models a biological tissue as a simple resistor-capacitor circuit. In this manner, the Cole model provides a characterization of the impedance of a biological tissue having the form:

$$\overline{Z} = \frac{Z_0 - Z_\infty}{1 + \left(\frac{j \cdot f}{f_c}\right)^\alpha} + Z_\infty,$$

Where $\overline{Z}$ is the impedance of the tissue; j is the complex number $j = \sqrt{-1}$; f is the applied measurement frequency in Hz; $f_c$ is the characteristic frequency for the electrical processes in the tissue under test; α is a real valued constant that typically ranges in value from 0 to 1; and $Z_0$ and $Z_\infty$ are complex numbers, wherein $Z_\infty$ is the limiting value of tissue impedance as the measuring frequency tends toward infinity and $Z_0$ is the limiting value of tissue impedance at lower frequencies.

The measured impedance values at the different frequencies are fit to the Cole model using a multidimensional, non-linear computer algorithm of Powell's method described in *Numerical Recipes*, Cambridge University Press. It should be appreciated by those skilled in the art, however, that many other curve fitting algorithms such as a non-linear least squares fitting methods could be equivalently employed to fit the impedance values to the Cole model. Additionally, other models of the impedance of biological tissues known in the art can be employed to practice the present invention. By fitting the impedance values for the tissues within the breast at each of the selected measurement frequencies to the Cole model, the characteristic frequency, $f_c$, for the modeled impedance values is determined, as indicated at step 402. The tissues within the breast are then characterized based on the determined characteristic frequency, $f_c$, as shown at step 404. The characterization process is performed by determining whether the characteristic frequency, $f_c$, value for a particular tissue is above a threshold value. If the characteristic frequency, $f_c$, of a tissue is above the threshold value of $10^5$ Hz (100 kHz), then the tissue is characterized as cancerous; however, if the characteristic frequency for the tissue is below $10^5$ Hz (100 kHz), then the tissue is characterized as being non-cancerous.

There exist some regions within the breast that exhibit more than one tissue type. For example, some regions are composed of fat in which blood vessels, milk ducts, or fibrous tissue are embedded or adjacent. In order to compensate for these mixtures of different tissue types, an alternative method fits the impedance values to a sum of two or more Cole type models. The overall functional dependence of the combined models is then used to determine one characteristic frequency, $f_c$, and the characterization process is carried out as described above.

The present invention has been described in terms of one or more preferred embodiments, and it should be appreciated that many equivalents, alternatives, variations, and modifications, aside from those expressly stated, are possible and within the scope of the invention. For example, the present invention can be used to detect cancerous regions in tissue types other than the breast Furthermore, other impedance measurement methods could be employed. For example, if an ex vivo examination is being performed on a tissue sample, then a time-domain reflectometer device could be employed. Furthermore, if an in vivo examination is being performed, impedance imaging systems and techniques other than EPET can be employed. Additionally, an EPET or other impedance imaging device could be integrated into a surgical probe and used to analyze different tissue types in vivo during a surgical procedure.

The invention claimed is:

1. A method for characterizing a tissue in a subject as cancerous or non-cancerous, the steps comprising:
    a) measuring an electrical property of the tissue at a selected frequency;
    b) repeating step a) a plurality of times to measure the electrical property of the tissue at a corresponding plurality of different selected frequencies;
    c) fitting the measured electrical properties of the tissue to a model of the electrical property of the tissue;
    d) determining, from the model, a characteristic frequency of the tissue;
    e) characterizing, by comparing the characteristic frequency of the tissue to a threshold, the tissue as one of at least cancerous and non-cancerous based on the relative value of the characteristic frequency compared to the threshold; and
    in which the threshold value is 100 kilohertz.

2. The method as recited in claim 1 in which step a) includes:
    applying a voltage to the subject;
    varying a magnitude of the applied voltage at the selected frequency;
    measuring a current resulting from the applied voltage; and
    determining the electrical property of the tissue from the applied voltage and the measured current.

3. The method as recited in claim 1 in which step a) includes:
    supplying a current to the subject;
    varying a magnitude of the supplied current at the selected frequency;
    measuring a voltage resulting from the supplied current; and
    determining the electrical property of the tissue from the supplied current and the measured voltage.

4. The method as recited in claim 1 in which each tissue is characterized as non-cancerous if the characteristic frequency of the tissue is below the threshold value.

5. The method as recited in claim 1 in which each tissue is characterized as cancerous if the characteristic frequency of the tissue is at or above the threshold value.

6. The method as recited in claim 1 in which the electrical property measured in step a) is an impedance.

7. The method as recited in claim 6 in which the model is a Cole model that models the impedance of the tissue as a function of the plurality of selected frequencies.

8. The method as recited in claim 1 in which step c) further includes fitting the measured electrical properties to a sum of at least two models.

9. The method as recited in claim 8 in which the electrical property measured in step a) is an impedance.

10. The method as recited in claim 9 in which at least one of the at least two models is a Cole model that models the impedance of the tissue as a function of the plurality of selected frequencies.

11. The method as recited in claim 1 in which the subject is a breast.

12. The method as recited in claim 1 in which the model is a Cole model that provides a characterization of the impedance of a biological tissue and the characterizing of step e) includes employing the Cole model.

13. The method as recited in claim 12 in which the Cole model has the form:

$$\overline{Z} = \frac{Z_0 - Z_\infty}{1 + \left(\frac{j \cdot f}{f_c}\right)^\alpha} + Z_\infty,$$

where $\overline{Z}$ is the impedance of the tissue; j is the complex number $j=\sqrt{-1}$; f is the applied measurement frequency in Hz; $f_c$ is the characteristic frequency for the electrical processes in the tissue under test; $\alpha$ is a real valued constant that typically ranges in value from 0 to 1; and $Z_0$ and $Z_\infty$ are complex numbers, wherein $Z_\infty$ is the limiting value of tissue impedance as the measuring frequency tends toward infinity, and $Z_0$ is the limiting value of tissue impedance at lower frequencies.

14. A method for characterizing a tissue in a subject as cancerous or non-cancerous, the steps comprising:
    a) measuring an electrical property of the tissue at a selected frequency;
    b) repeating step a) a plurality of times to measure the electrical property of the tissue at a corresponding plurality of different selected frequencies;
    c) fitting the measured electrical properties of the tissue to a Cole model of the electrical property of the tissue;
    d) determining, from the Cole model, a characteristic frequency of the tissue;
    e) characterizing, from the characteristic frequency, the Cole model, and a threshold, the tissue as one of at least cancerous and non-cancerous;
    in which the threshold value is 100 kilohertz.

15. The method as recited in claim 14 in which the Cole model provides a characterization of the impedance of a biological tissue having the form:

$$\overline{Z} = \frac{Z_0 - Z_\infty}{1 + \left(\frac{j \cdot f}{f_c}\right)^\alpha} + Z_\infty,$$

where $\overline{Z}$ is the impedance of the tissue; j is the complex number $j=\sqrt{-1}$; f is the applied measurement frequency in Hz; $f_c$ is the characteristic frequency for the electrical processes in the tissue under test; $\alpha$ is a real valued constant that typically ranges in value from 0 to 1; and $Z_0$ and $Z_\infty$ are complex numbers, wherein $Z_\infty$ is the limiting value of tissue impedance as the measuring frequency tends toward infinity, and $Z_0$ is the limiting value of tissue impedance at lower frequencies.

16. The method as recited in claim 14 in which step a) includes:
   applying a voltage to the subject;
   varying a magnitude of the applied voltage at the selected frequency;
   measuring a current resulting from the applied voltage; and
   determining the electrical property of the tissue from the applied voltage and the measured current.

* * * * *